(12) United States Patent
Yoon et al.

(10) Patent No.: US 8,322,469 B2
(45) Date of Patent: Dec. 4, 2012

(54) BIDIRECTIONAL MOVING MICRO-ROBOT SYSTEM

(75) Inventors: Eui Sung Yoon, Seoul (KR); Sung Wook Yang, Gyeonggi-do (KR); Jin Seok Kim, Seoul (KR); Kyoung Hwan Na, Gyeonggi-do (KR); Duk Moon Rho, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 181 days.

(21) Appl. No.: 12/847,851

(22) Filed: Jul. 30, 2010

(65) Prior Publication Data

US 2011/0214927 A1    Sep. 8, 2011

(30) Foreign Application Priority Data

Mar. 5, 2010   (KR) ........................ 10-2010-0019769

(51) Int. Cl.
  *B25J 5/00*   (2006.01)
(52) U.S. Cl. ........... 180/7.1; 180/7.2; 600/141; 600/152
(58) Field of Classification Search .................... 180/7.1; 600/141, 152; 104/138.2
See application file for complete search history.

(56) References Cited

U.S. PATENT DOCUMENTS

| 5,906,591 | A | 5/1999 | Dario et al. |
|---|---|---|---|
| 6,162,171 | A | 12/2000 | Ng et al. |
| 6,520,272 | B2 * | 2/2003 | Cho et al. ........................ 180/8.1 |
| 6,824,508 | B2 * | 11/2004 | Kim et al. ........................ 600/101 |
| 6,911,004 | B2 * | 6/2005 | Kim et al. ........................ 600/101 |
| 7,365,509 | B2 | 4/2008 | Park et al. |
| 2006/0257234 | A1 | 11/2006 | Park et al. |

FOREIGN PATENT DOCUMENTS

| KR | 10-2005-0104023 | 11/2005 |
|---|---|---|
| KR | 10-2006-0117110 | 11/2006 |
| KR | 10-0839546 | 6/2008 |

OTHER PUBLICATIONS

PCT International Search Report, PCT Application No. PCT/KR2010/004576, Apr. 1, 2011, three pages.

* cited by examiner

*Primary Examiner* — Tashiana Adams
*Assistant Examiner* — Michael Stabley
(74) *Attorney, Agent, or Firm* — Fenwick & West LLP

(57) ABSTRACT

Disclosed herein is a bidirectional moving micro-robot system. The bidirectional moving micro-robot system has a first body having a plurality of legs foldably/unfoldably connected thereto, a second body having a plurality of legs foldably/unfoldably connected thereto and a connection member having both end portions respectively connected to the first and second bodies. In the bidirectional moving micro-robot system, the length of the connection member exposed between the first and second bodies is extended or contracted.

9 Claims, 17 Drawing Sheets

BIDIRECTIONAL MOVING MICRO-ROBOT SYSTEM

CROSS-REFERENCE TO RELATED APPLICATION

This application claims priority to Korean Patent Application No. 10-2010-0019769, filed on Mar. 5, 2010, and all the benefits accruing therefrom under 35 U.S.C. §119, the contents of which in its entirety are herein incorporated by reference.

BACKGROUND

1. Field of the Invention

Disclosed herein is a bidirectional moving micro-robot system. More particularly, disclosed herein is a bidirectional moving micro-robot system capable of moving bidirectionally, i.e., forward and backward, in the inside of internal organs.

2. Description of the Related Art

A method using an endoscope is used as a method for treating or examining internal organs in vivo without cutting them open. However, such a typical endoscopic method requires a highly skilled operating technique and gives patients pain.

Therefore, technologies for an in-vivo movement system have been studied, which is inserted into a patient's body through its mouth or anus to treat or examine internal organs without giving the patient pain. A capsule type endoscope that is inserted into a human body through its mouth to photograph the inside of the human body is used as a representative in-vivo movement system.

The capsule type endoscope is provided with a microminiature camera for photographing in-vivo images, a communication device for transmitting the photographed images to the exterior thereof, and the like. Through the capsule type endoscope, it is possible to photograph the inside of internal organs.

However, since such a capsule type endoscope passively moves in an internal organ in dependent upon the peristalsis of the internal organ, its moving speed is entirely slow in the internal organ and remarkably changed depending on characteristics of a digestive organ or patients subjected to operation. Further, since the in-vivo position and pose of the capsule type endoscope are not appropriately controlled depending on conditions, it is difficult to make an accurate diagnosis.

Therefore, studies have been conducted to develop a robot system that is provided a moving unit of its own to actively move in the inside of internal organs. However, it is general that active-moving type robot systems that have been developed so far can move only in one direction.

Such a unidirectional moving robot system has difficulty in moving backward to perform a desired operating or photographing process when it passes by an affected part or part necessary for photographing. A bidirectional moving micro-robot system has been developed to solve such a problem. However, the structure of the system is complicated, and it is difficult to control the system.

SUMMARY OF THE INVENTION

Disclosed herein is a bidirectional moving micro-robot system which can be easily controlled with a simple structure and move forward and backward in the inside of internal organs.

In an aspect, there is provided a bidirectional moving micro-robot system including a first body having a plurality of legs foldably/unfoldably connected thereto; a second body having a plurality of legs foldably/unfoldably connected thereto; and a connection member having both end portions respectively connected to the first and second bodies. The length of the connection member exposed between the first and second bodies is extended or contracted.

The connection member may be flexibly bent.

The connection member may be a coil-type spring.

The first body may include a motor having a body and a shaft, and the operation of folding/unfolding the plurality of legs provided to the first body and the operation of extending/contracting the length of the connection member may be performed by the movement of the motor.

The first body may include a first cylinder connected to the motor to surround the body of the motor; and a cover for accommodating the motor and the first cylinder in the interior thereof. In the first body, a plurality of leg latching grooves may be formed at an outer circumferential surface of the first cylinder. The plurality of legs connected to the first body may be radially disposed about the central axis of the first body, and each of the legs may be hinge-fixed to the cover. As the first cylinder is rotated by the rotation of the body of the motor, an end portion of each of the legs connected to the first body may be latched by the interference of each of the leg latching groove so that the legs are folded or unfolded.

The first body may further include a second cylinder connected to the motor to surround the body of the motor. A key may be formed to protrude from an outer circumferential surface of the second cylinder. A key groove engaged with the key may be formed at an inner circumferential surface of the cover. The width of the key groove may be wider than that of the key.

A spring screw having a screw thread formed on an outer circumferential surface thereof may be connected to the shaft of the motor. The coil-type spring may be fastened to the spring screw. As the coil-type spring is moved along the screw thread of the spring screw by the rotation of the shaft of the motor, the length of the connection member may be controlled.

An anti-rotation groove may be formed in the length direction of the cover at the inner circumferential surface of the cover, and an anti-rotation projection engaged with the anti-rotation groove may be formed at each end of the coil-type spring.

When the length of the connection member is contracted, a portion of the coil-type spring may be accommodated into the interior of the cover.

The structure of the second body may be identical to that of the first body, and the first and second bodies may be disposed to be symmetric to each other about the connection member.

The length of the connection member may be controlled by the motor provided to the first body when the bidirectional moving micro-robot system is moved forward, and the length of the connection member may be controlled by the motor provided to the second body when the bidirectional moving micro-robot system is moved backward.

BRIEF DESCRIPTION OF THE DRAWINGS

The above and other aspects, features and advantages of the present invention will become apparent from the following description of preferred embodiments given in conjunction with the accompanying drawings, in which.

DETAILED DESCRIPTION OF THE INVENTION

Figure 1:
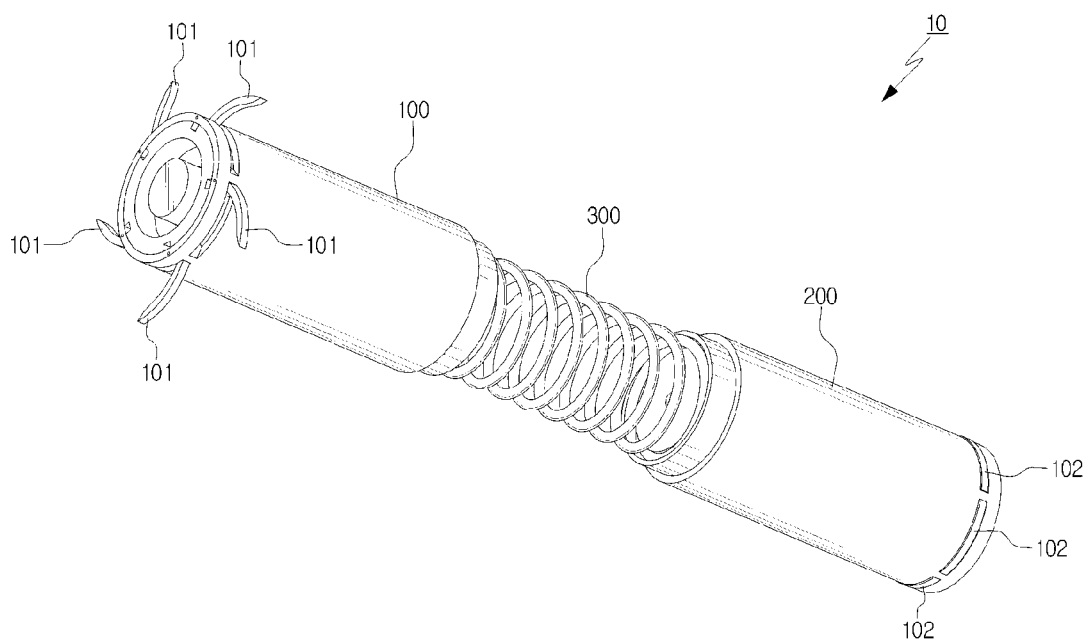
FIG. 1 is a perspective view of a bidirectional moving micro-robot system 10 according to an embodiment.

Exemplary embodiments now will be described more fully hereinafter with reference to the accompanying drawings, in which exemplary embodiments are shown. This disclosure may, however, be embodied in many different forms and should not be construed as limited to the exemplary embodiments set forth therein. Rather, these exemplary embodiments are provided so that this disclosure will be thorough and complete, and will fully convey the scope of this disclosure to those skilled in the art. In the description, details of well-known features and techniques may be omitted to avoid unnecessarily obscuring the presented embodiments.

The terminology used herein is for the purpose of describing particular embodiments only and is not intended to be limiting of this disclosure. As used herein, the singular forms "a", "an" and "the" are intended to include the plural forms as well, unless the context clearly indicates otherwise. Furthermore, the use of the terms a, an, etc. does not denote a limitation of quantity, but rather denotes the presence of at least one of the referenced item. The use of the terms "first", "second", and the like does not imply any particular order, but they are included to identify individual elements. Moreover, the use of the terms first, second, etc. does not denote any order or importance, but rather the terms first, second, etc. are used to distinguish one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

In the drawings, like reference numerals in the drawings denote like elements. The shape, size and regions, and the like, of the drawing may be exaggerated for clarity.

FIG. 1 is a perspective view of a bidirectional moving micro-robot system 10 according to an embodiment.

As illustrated in FIG. 1, the robot system 10 includes first and second bodies 100 and 200 having a cylindrical shape. A connection member 300 is positioned between the first and second bodies 100 and 200. Both end portions of the connection member 300 are joined with the first and second bodies 100 and 200, respectively.

A plurality of first legs 101 are foldably/unfoldably connected to the first body 100, and a plurality of second legs 201 are foldably/unfoldably connected to the second body 200. In FIG. 1, the first legs 101 are in the state that they are unfolded with respect to the first body 100, and the second legs 201 are in the state that they are unfolded with respect to the second body 200. As illustrated in FIG. 1, the connection member 300 according to this embodiment is a coil-type spring.

Figure 2:
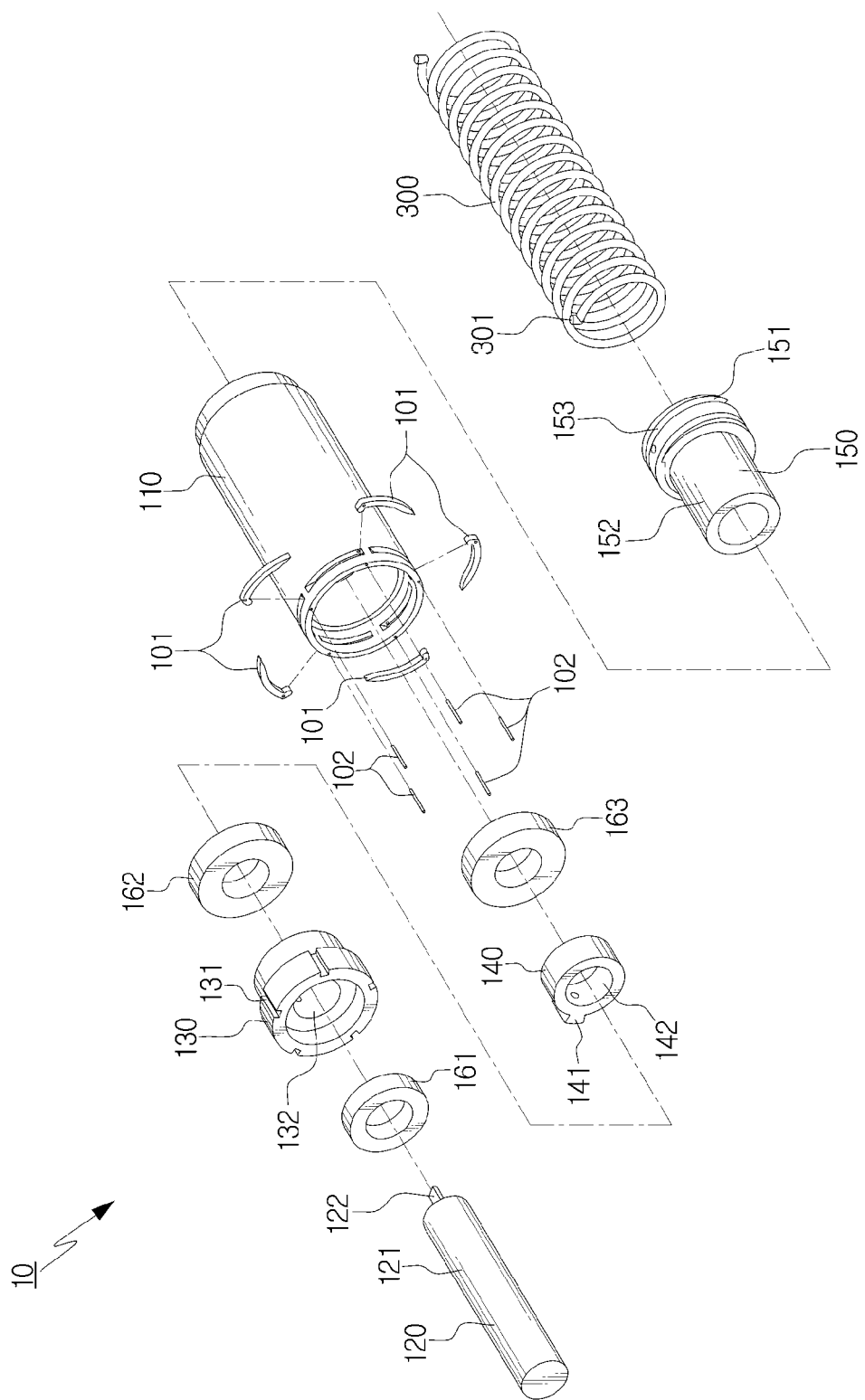
FIG. 2 is an exploded perspective view of the bidirectional moving micro-robot system 10 according to this embodiment.

FIG. 2 is an exploded perspective view of the bidirectional moving micro-robot system 10 according to this embodiment. In FIG. 2, the second body 200 is omitted.

As illustrated in FIG. 2, the first body 100 includes a cylinder-shaped cover 110 having a void formed therein. The first legs 101 are radially disposed about the central axis of the first body 100. Each of the first legs 101 is hinge-fixed to the cover 110 by a pin 102. Through the aforementioned configuration, the first legs 101 can be folded and unfolded in a radial shape with respect to the cover 110 (see FIG. 1).

Through-holes 111 having the same number as that of the first legs 101 are formed at an end portion of one side of the cover 110. When the first legs 101 are folded, they are accommodated into the cover 110 through the respective through-holes 111 (see the second legs 201 of FIG. 1).

The first body 100 includes a motor 120, a first cylinder 130, a second cylinder 140 and a spring screw 150. The first body 100 is provided with three bearings 161, 162, 163.

The motor 120 includes a body 121 and a shaft 122. A through-hole 132 is formed at the center of the first cylinder 130, and a plurality of leg latching grooves 131 formed in the length direction of the first body 100 are formed at the outer circumferential surface of the first cylinder 130. In this embodiment, the number of the leg latching grooves 131 is identical to that of the first legs 101.

A through hole 142 is formed at the center of the second cylinder 140, and a key 141 is formed to protrude from the outer circumferential surface of the second cylinder 140. The spring screw 150 has an approximately "T" shape and includes a head portion 151 and a body portion 152. A screw thread 153 is formed at the outer circumferential surface of the head portion 151, and the connection member 300 that is a coil-type spring is engaged with the screw thread 153.

Hereinafter, the joining relationships between the aforementioned components of the first body 100 will be described in detail with reference to FIGS. 3A and 3B.

Figure 3A:
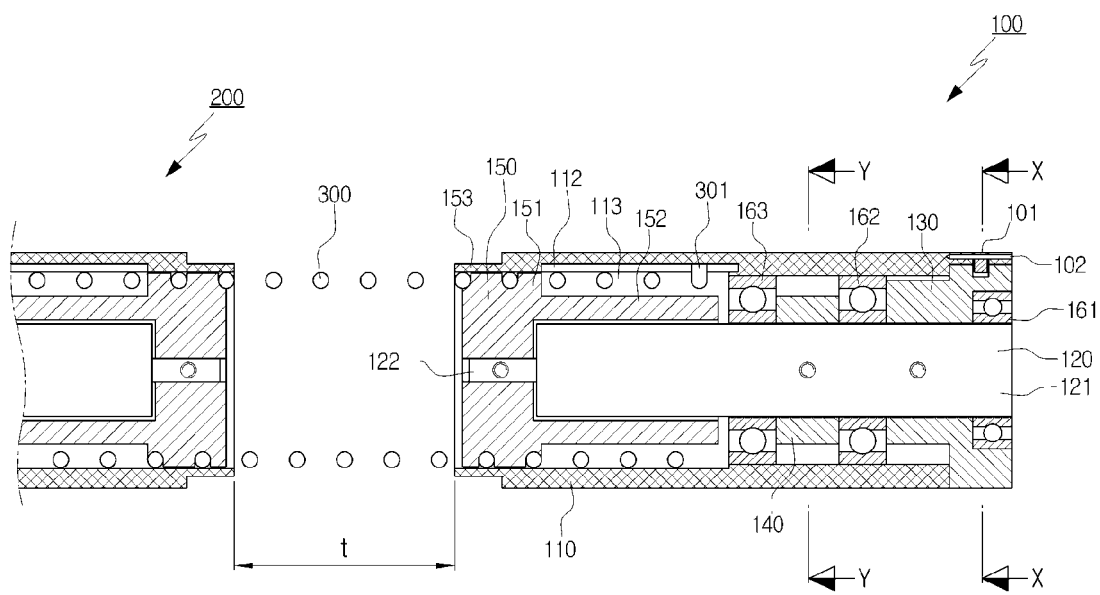
FIGS. 3A and 3B are plan sectional view of the robot system 10 according to this embodiment.
Figure 3B:
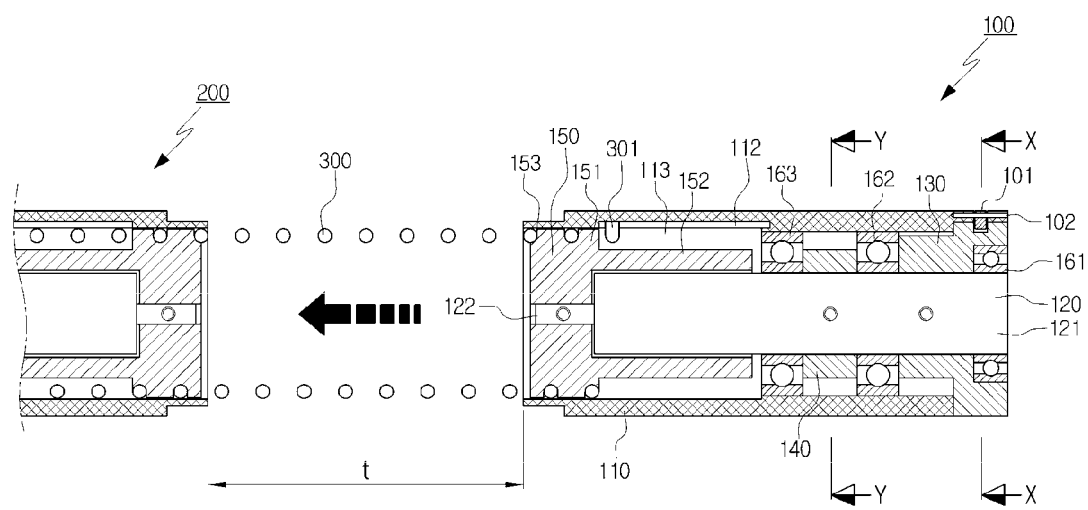

FIGS. 3A and 3B are plan sectional view of the robot system 10 according to this embodiment.

Referring to FIGS. 3A and 3B, the motor 120, the first cylinder 130, the second cylinder 140 and the spring screw 150 are accommodated in the interior of the cover 110. The shaft 122 of the motor 120 is disposed to face toward the second body 200.

The first cylinder 130 is connected to the motor 120 through the through-hole 132 to surround the body 121 of the motor 120. The first cylinder 130 is fixed to the body 121 of the motor 120 so as not to be freely rotatable.

The second cylinder 140 is connected to the motor 120 through the through-hole 142 to surround the body 121 of the motor 120. The second cylinder 140 is fixed to the body 121 of the motor 120 so as not to be freely rotatable.

The two bearings 162 and 163 are disposed at both sides about the second cylinder 140 to be connected the body 121 of the motor 120.

As illustrated in FIGS. 3A and 3B, the spring screw 150 is connected to the shaft 122 of the motor 120 through a through-hole formed at the head portion 151 thereof. The body portion 152 of the spring screw 150 is configured to surround a portion of the body 121 of the motor 120, and the inner circumferential surface of the body portion 152 is not adhered closely to the body 121 of the motor 120 but spaced apart from the body 121 of the motor 120 at a predetermined interval. Therefore, if the shaft 122 is rotated by the motor 120, the spring screw 150 is rotated together with the shaft 122.

Since the spring screw 150 has an approximately "T" shape, a space 113 is formed between the cover 110 and the body portion 152 of the spring screw 150.

Meanwhile, the screw thread 153 is formed at the outer circumferential surface of the head portion 151 of the spring screw 150, and the connection member 300 is engaged with the screw thread 153. An anti-rotation projection 301 (see FIG. 2) is formed at each end of the connection member 300, and an anti-rotation groove 112 is formed in a line along the length direction of the cover 110 at the inner circumferential surface of the cover 110. The anti-rotation projection 301 is engaged with the anti-rotation groove 112.

According to the aforementioned configuration, if the shaft 122 of the motor 120 is rotated, the spring screw 150 is rotated together with the shaft 122 of the motor 120 as illustrated in FIGS. 3A and 3B. Since the anti-rotation projection 310 is engaged with the anti-rotation groove 112, the connection member 300 is not rotated together with the spring screw 150 but straightly moved in a forward or backward direction.

If the connection member 300 is moved in a left direction by driving the motor 120 in the state that a portion of the connection member 300 is accommodated in the space 113 as illustrated in FIG. 3A, the length t of the connection member 300 exposed between the first and second bodies 100 and 200 is extended as illustrated in FIG. 3B.

On the contrary, if the connection member 300 is moved in a right direction by driving the motor 120 in the state illustrated in FIG. 3B, the length t of the connection member 300 exposed between the first and second bodies 100 and 200 is contracted while a portion of the connection member 300 is accommodated in the space 113 within the cover 110. That is, the length of the connection member 300 exposed between the first and second bodies 100 and 200 is extended or contracted by the rotation of the shaft 122 of the motor 120.

Figure 4:
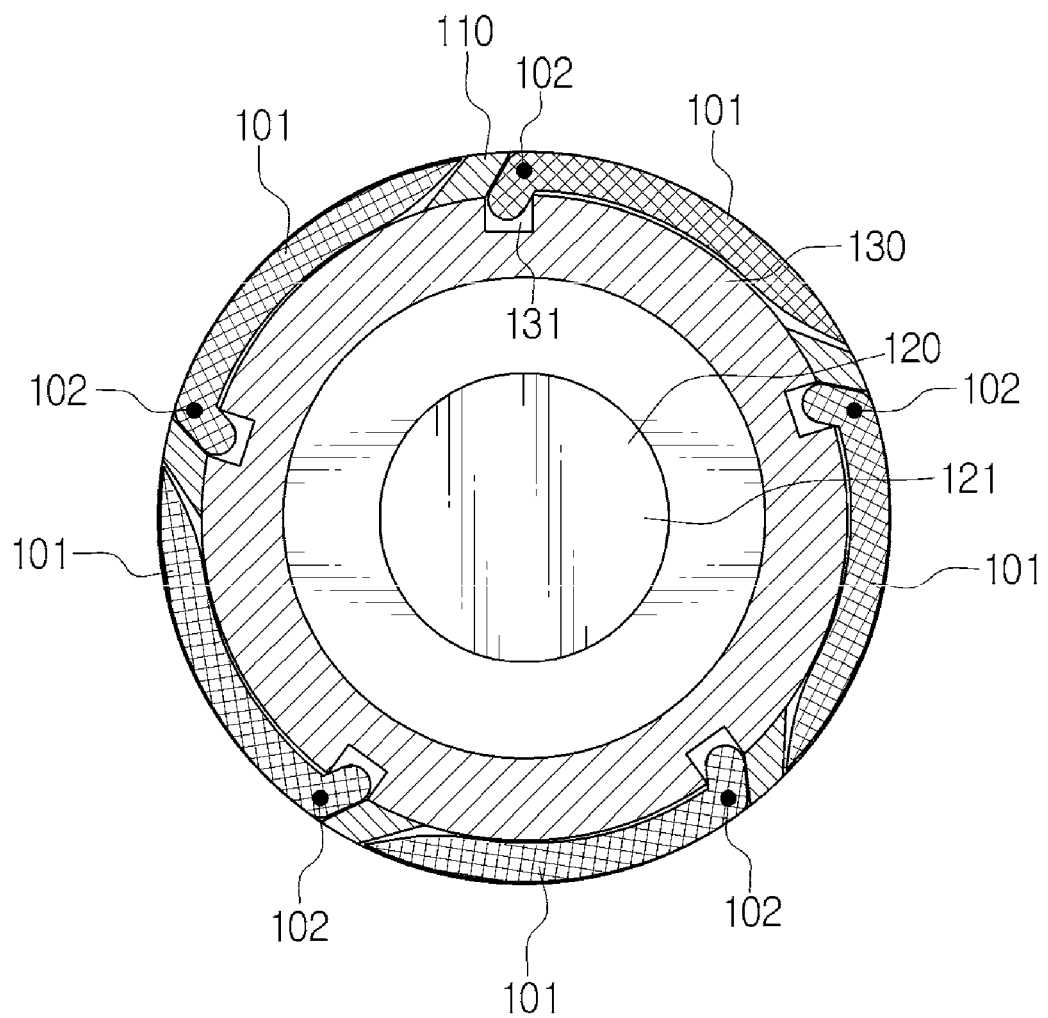
FIG. 4 is a cross-sectional view taken along line X-X of FIGS. 3A and 3B.

FIG. 4 is a cross-sectional view taken along line X-X of FIGS. 3A and 3B.

As illustrated in FIG. 4, the leg latching grooves 131 are formed at the outer circumferential of the first cylinder 130. Here, the leg latching grooves 131 are vertically formed to have an approximately square section. Each of the first legs 101 has one end portion bent at a predetermined angle, and the bent portion is engaged with each of the leg latching grooves 131.

Figure 5:
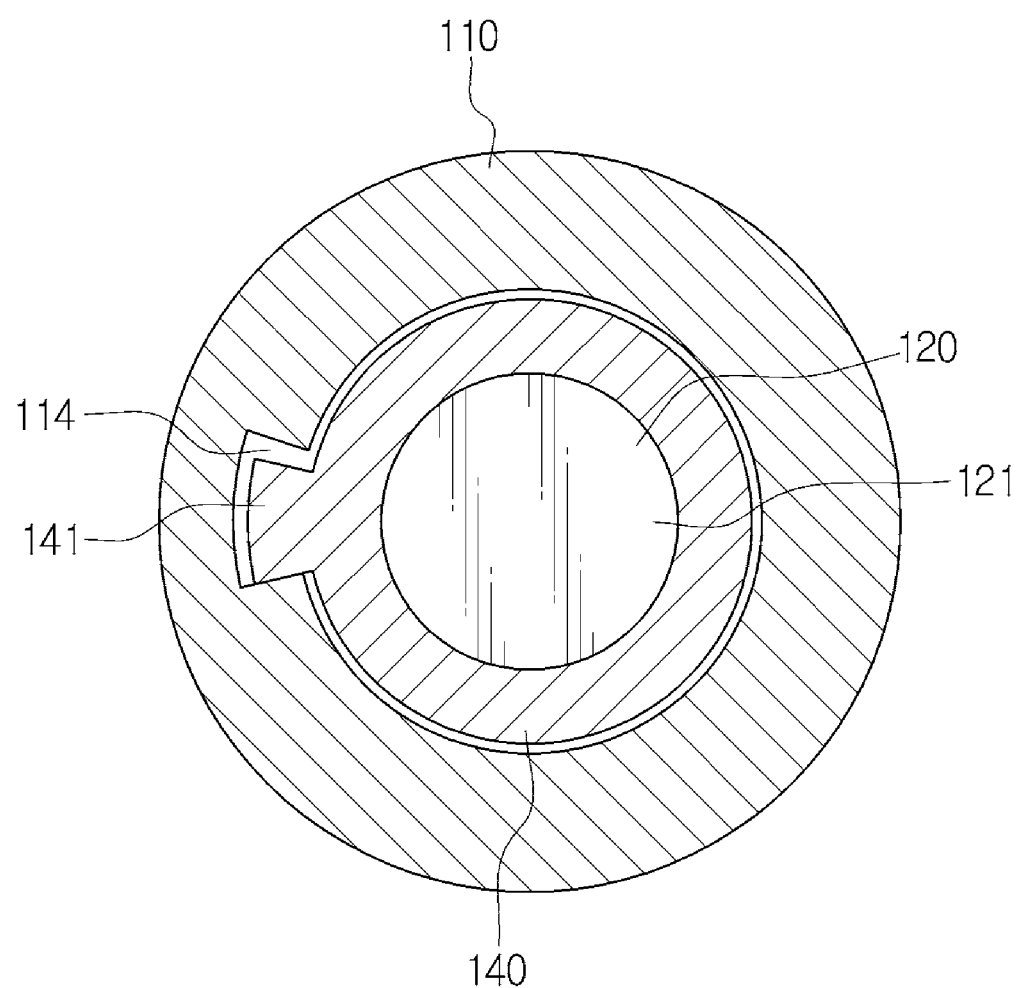
FIG. 5 is a cross-sectional view taken along line Y-Y of FIGS. 3A and 3B.

FIG. 5 is a cross-sectional view taken along line Y-Y of FIGS. 3A and 3B.

As illustrated in FIG. 5, a key groove 114 is formed at the inner circumferential surface of the cover 110, and the key 141 formed at the second cylinder 140 is engaged with the key groove 114. The width of the key groove 114 is formed wider than that of the key 141.

According to this embodiment, the first legs 101 are unfolded or folded by the rotation of the body 121 of the motor 120.

Hereinafter, the principle in which the first legs 101 perform folding and unfolding operations will be described with reference to FIGS. 6A, 6B, 7A and 7B.

Figure 6A:
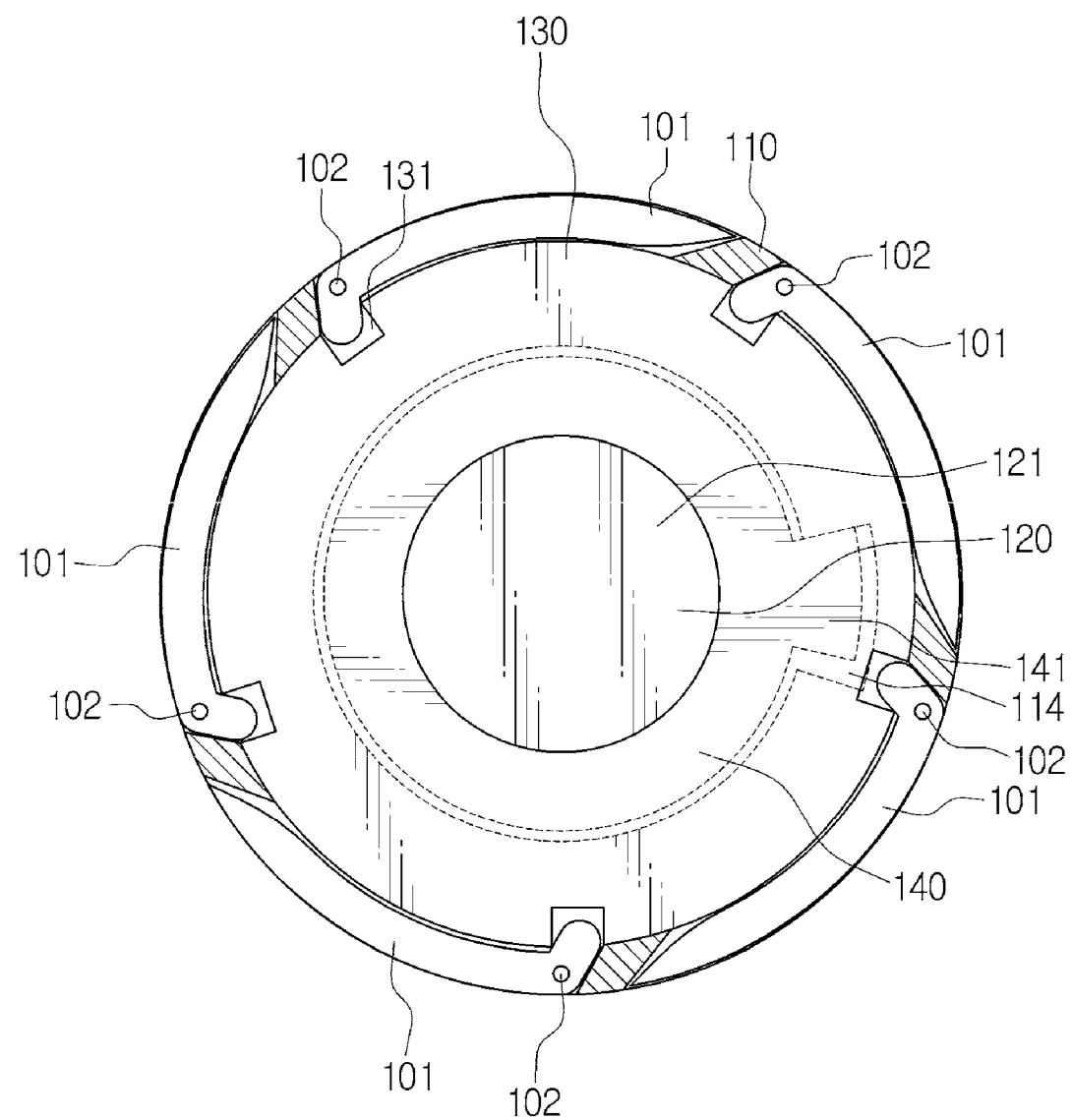
FIGS. 6A and 6B are views illustrating an operation in which first legs 101 are unfolded.
Figure 6B:
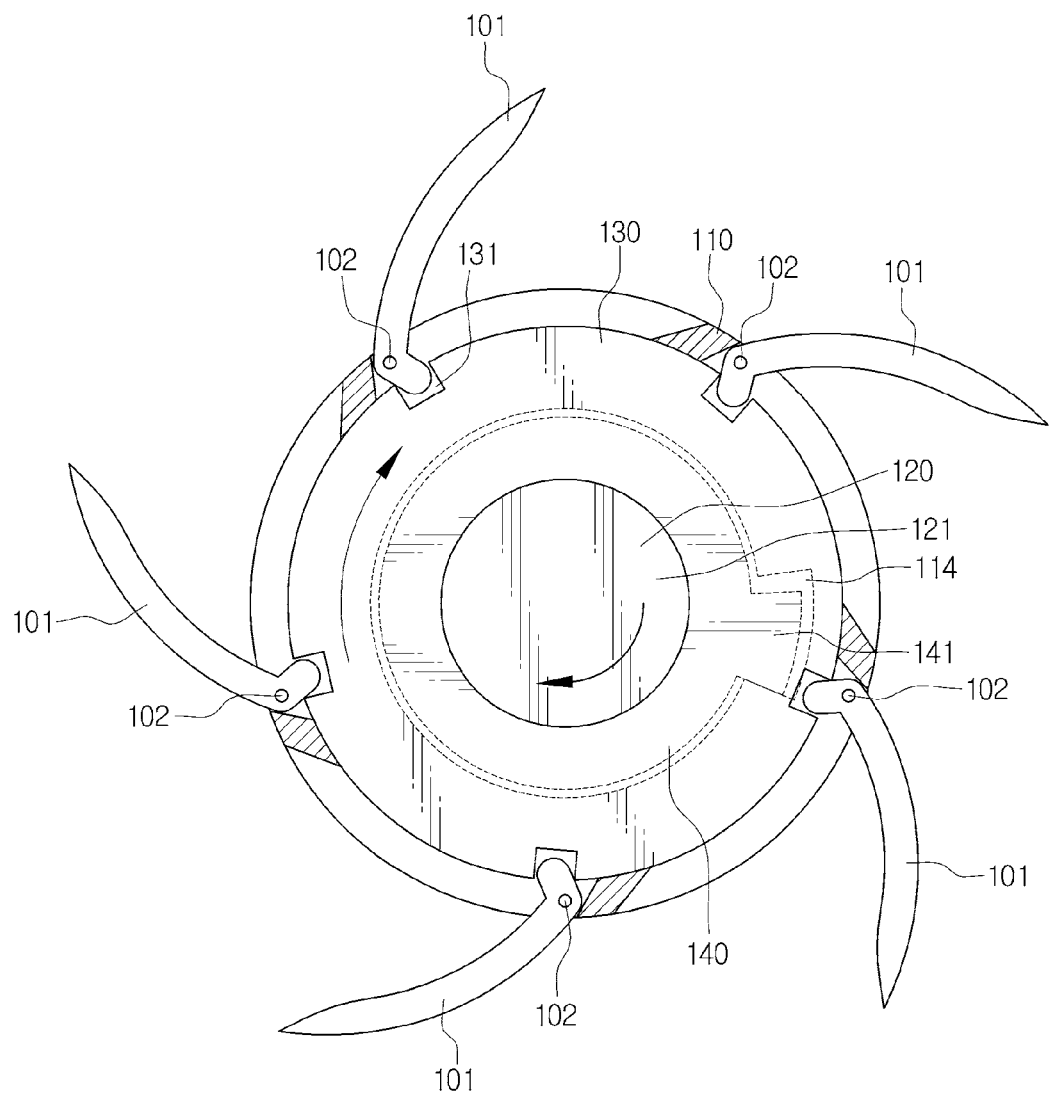

FIGS. 6A and 6B are views illustrating an operation in which the first legs 101 are unfolded.

As described above, the first cylinder 130 is connected to the body 121 of the motor 120 so as not to be freely rotatable. Therefore, if the body 121 of the motor 120 is rotated clockwise, the first cylinder 130 is also rotated clockwise as illustrated in FIG. 6B.

If the first cylinder 130 is rotated clockwise, an end portion of the first leg 101, engaged with the leg latching groove 131, is pushed by the interference of the leg latching groove 131. The first leg 101 is hinge-fixed to the cover 110 by the pin 102. Therefore, if the leg latching groove 131 pushes the end portion of the first legs 101, the first leg 101 is unfolded while turning about the pin (hinge point) 102.

Figure 7A:
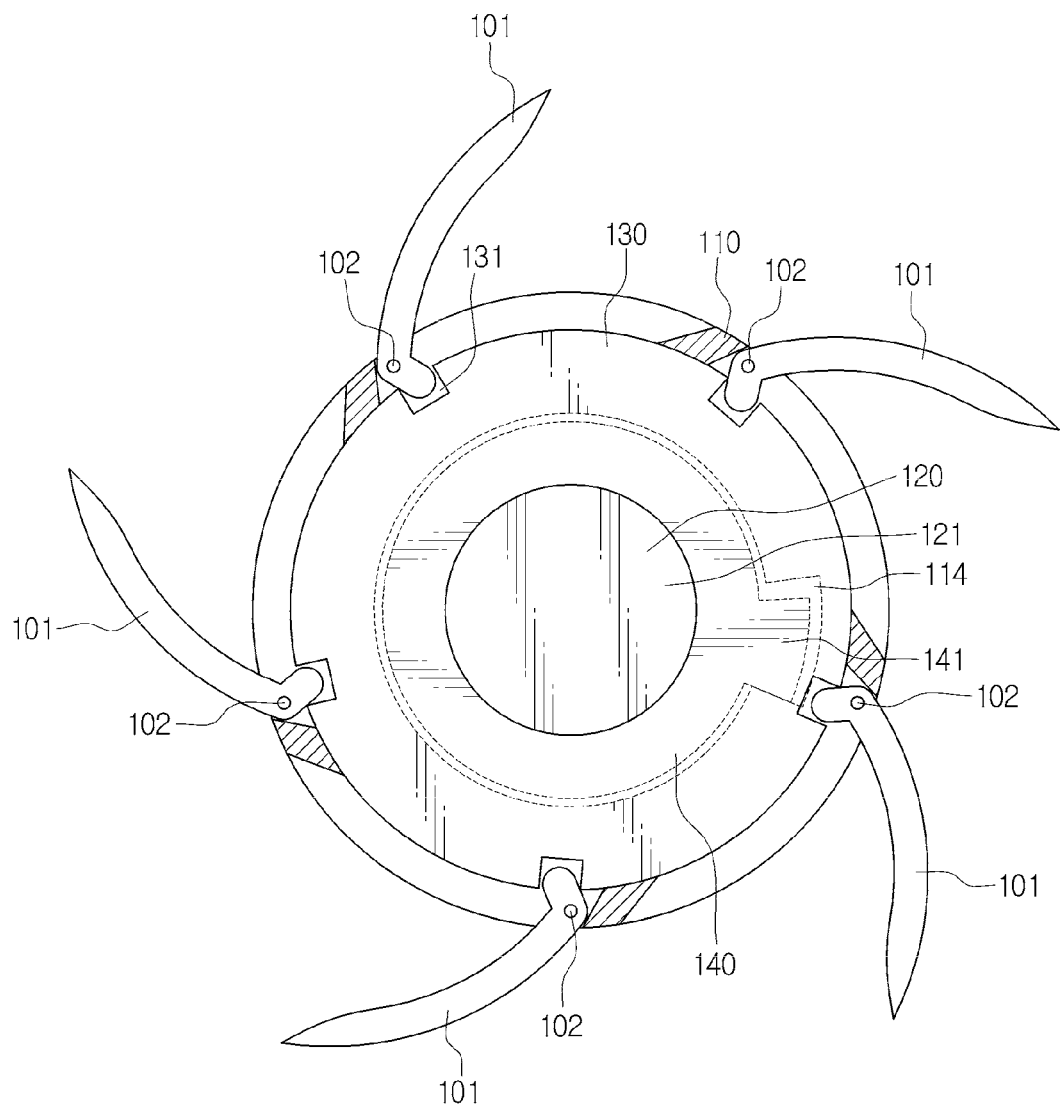
FIGS. 7A and 7B are conceptual views illustrating a principle in which the first legs 101 are folded.
Figure 7B:
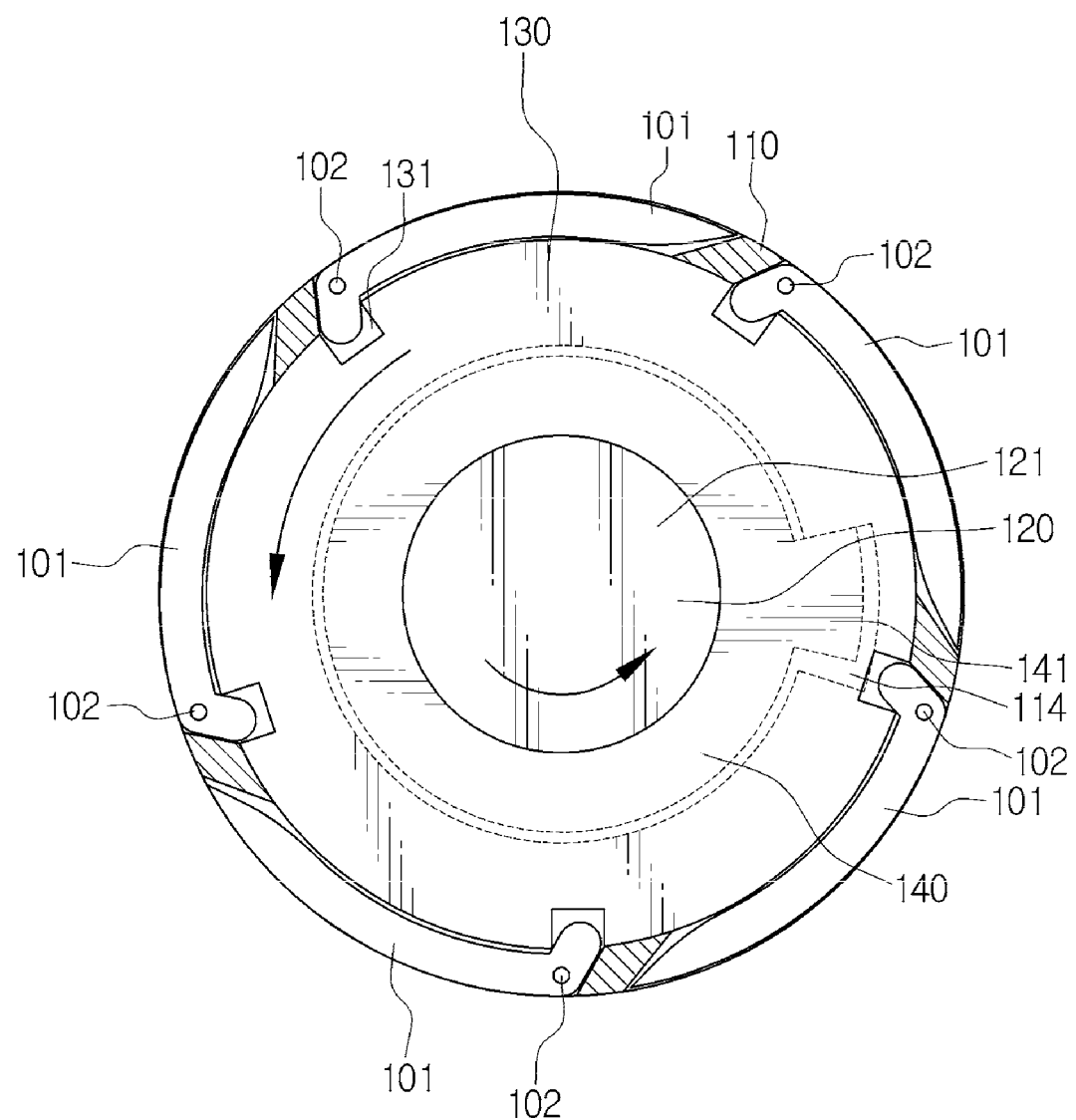

FIGS. 7A and 7B are conceptual views illustrating a principle in which the first legs 101 are folded.

On the contrary to the operation in which the first legs 101 are unfolded, if the body 121 of the motor 120 is rotated counterclockwise, the end portion of the first leg 101 is unfolded by the interference of the leg latching groove as illustrated in FIGS. 7A and 7B.

According to this embodiment, while the first legs 101 are folded or unfolded by the rotation of the body 121 of the motor 120, the length of the connection member 300 exposed between the first and second bodies 100 and 200 is extended or contracted by the rotation of the shaft 122 of the motor 120.

Meanwhile, according to this embodiment, the structure of the second body 200 is identical to that of the first body 100 described above. As illustrated in FIG. 1, the first and second bodies 100 and 200 are disposed to be symmetric to each other about the connection member 300.

Thus, the robot system 10 according to this embodiment can be bidirectionally moved by appropriately controlling the motors respectively provided to the first and second bodies 100 and 200.

Hereinafter, the principle in which the robot system 10 performs bidirectional moving operations according to this embodiment will be described with reference to FIGS. 8A to 9G. For convenience of illustration, the covers of the first and second bodies 100 and 200 are transparently and simply shown in FIGS. 8A to 9G. The bearings 162 and 163 will also be omitted.

FIGS. 8A, 8B, 8C, 8D, 8E, 8F, and 8G are perspective views illustrating an operation in which the robot system 10 is moved forward according to this embodiment.

Figure 8A:
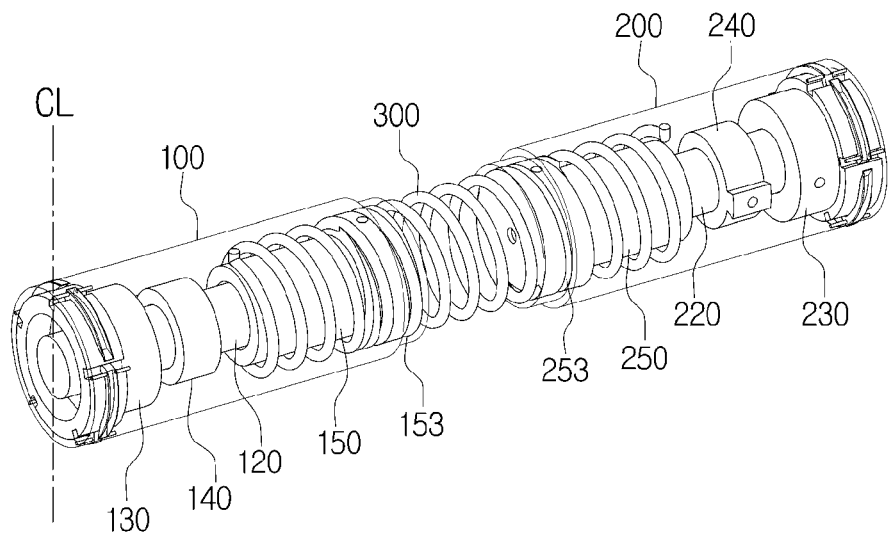
FIGS. 8A, 8B, 8C, 8D, 8E, 8F, and 8G are perspective views illustrating an operation in which the robot system 10 is moved forward according to this embodiment.
Figure 8B:
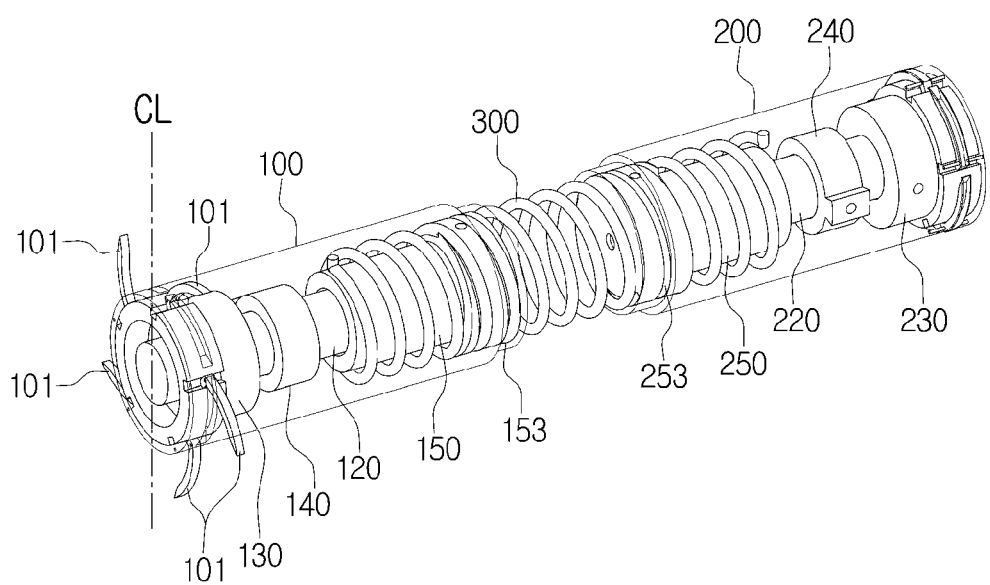

As illustrated in FIG. 8A, power for rotating the shaft of the motor 120 of the first body 100 counterclockwise is provided to the motor 120 so that the robot system 10 in an initial state is moved forward. At this time, a frictional force acts between the connection member 300 and the screw thread 153, and therefore, the rotation of the shaft of the motor 120 of the first body 100 is constrained by a predetermined force. Therefore, if the power for rotating the shaft of the motor 120 of the first body 100 is provided to the motor, the body of the motor 120 is relatively rotated clockwise. If the body 120 of the motor 120 is rotated, the first cylinder 130 is rotated together. Thus, through the principle in which the first legs 101 are unfolded (see FIGS. 6A and 6B), the first legs 101 are unfolded to support an inner wall of an internal organ (not shown) as illustrated in FIG. 8B.

Meanwhile, if the body of the motor 120 is rotated, the second cylinder 140 is rotated together. Therefore, the key 141 adhered closely to the left wall of the key groove 114 as illustrated in FIG. 6A is adhered closely to the right wall of the key groove 114 as illustrated in FIG. 6B. As such, if the key 141 is adhered closely to the right wall of the key groove 114, the second cylinder 140 is not rotated any more, and therefore, the rotation of the second cylinder 140 is constrained. If the second cylinder 140 is not rotated any more, and therefore, the rotation of the second cylinder 140 is constrained, the body of the motor 120 fixed to the second cylinder 140 is also not rotated any more, and therefore, the rotation of the second cylinder 140 is constrained.

In this case, if the power for rotating the shaft of the motor 120 of the first body 100 counterclockwise is continuously provided to the motor 120, the body of the motor 120 is not rotated any more. Therefore, the shaft of the motor 120 exceeds the frictional force between the connection member 300 and the screw thread 153 and thus is rotated counterclockwise. As the shaft of the motor 120 is rotated, the spring screw 150 is rotated counterclockwise together with the motor 120. In this embodiment, when the shaft of the motor 120 is rotated counterclockwise, the spiral direction of the screw thread 153 formed at the spring screw 150 is formed so that the connection member 300 can be moved in a forward direction (i.e., a direction distant from the second cylinder 140).

Figure 8C:
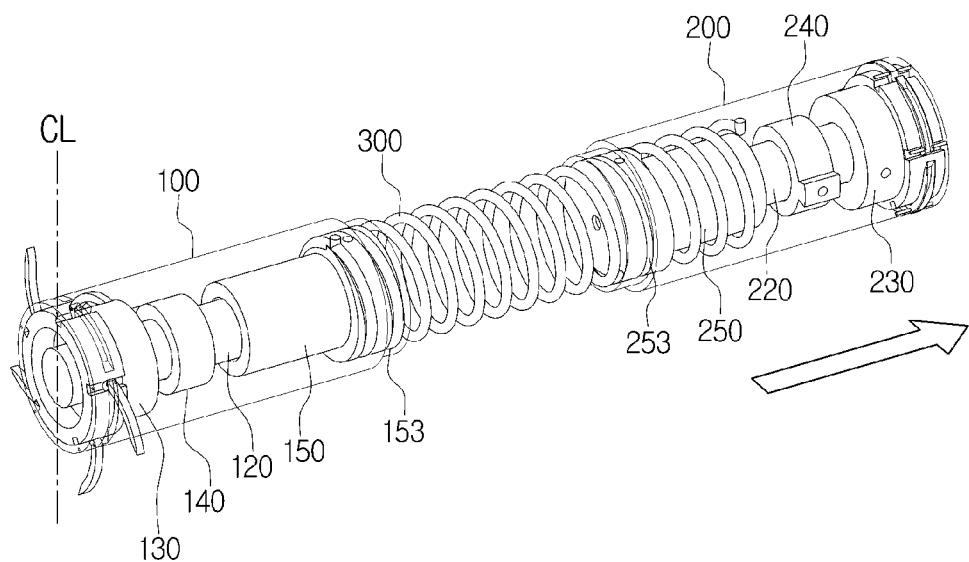

Thus, if the spring screw 150 is rotated counterclockwise, the connection member 300 is moved forward along the screw thread 153 formed at the spring screw 150, and thus, the length of the connection member 300 exposed between the first and second bodies 100 and 200 is extended as illustrated in FIG. 8C (see the above descriptions regarding FIGS. 3A and 3B). If the length of the connection member 300 is extended, the second body 200 connected to an end portion of the connection member 300 is moved forward in the arrow direction together with the connection member 300.

Figure 8D:
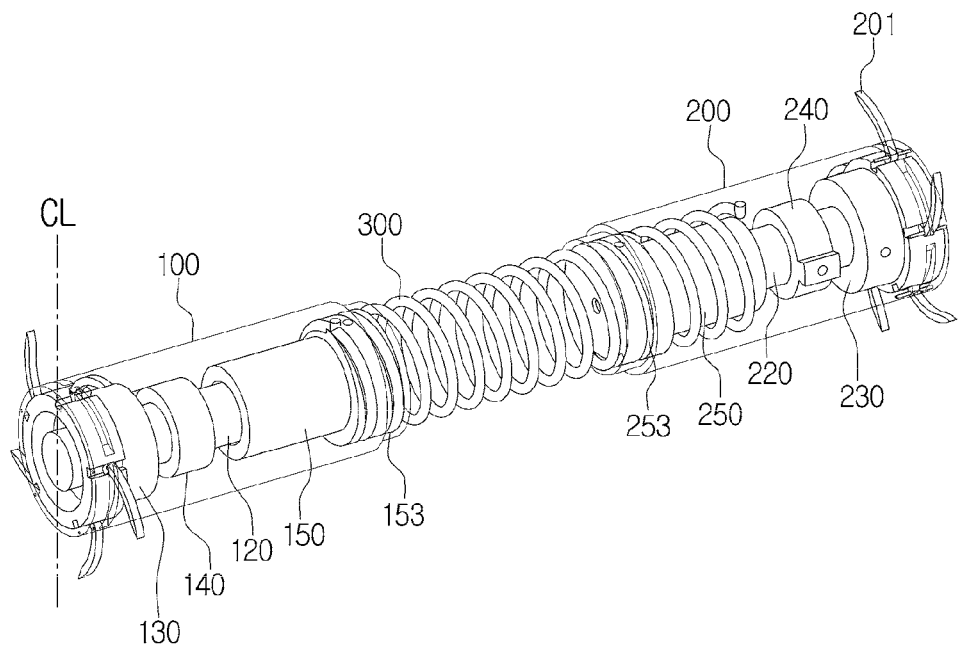
Figure 8E:
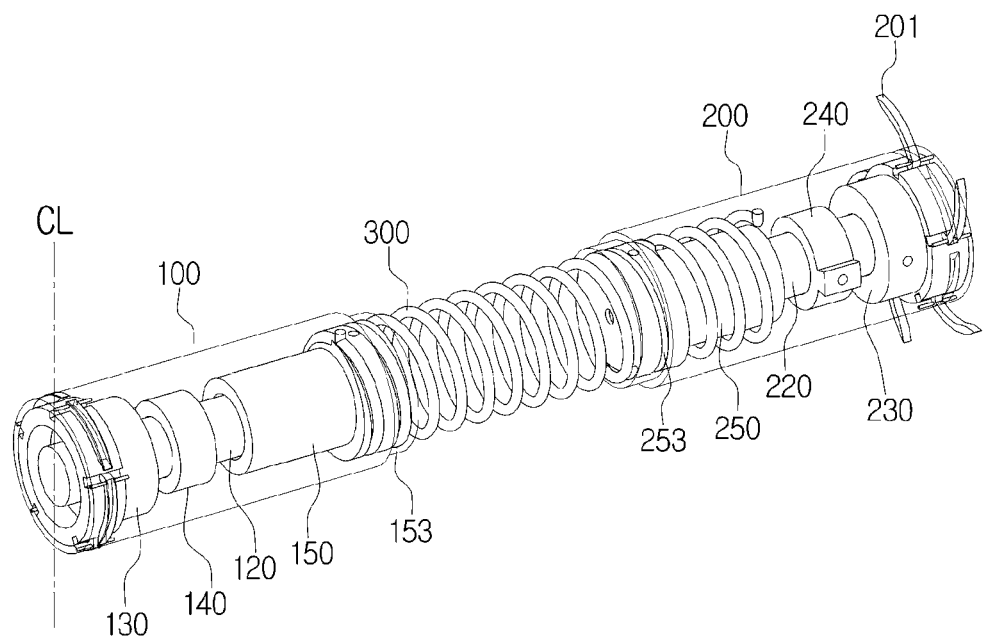

If the connection member 300 is completely extended, the second legs 201 are unfolded by driving a motor 220 provided to the second body 200 as illustrated in FIG. 8D. In this embodiment, since the structure of the second body 200 is identical to that of the first body 100, the principle in which the second legs 201 are unfolded is identical to that in which the first legs 101 are unfolded.

If the second legs 201 are unfolded, they support an inner wall of the internal organ (not shown). In this state, power for rotating the shaft of the motor 120 of the first body 100 clockwise is provided to the motor 120. Here, the frictional force acts between the connection member 300 and the screw thread 153. Therefore, if the power for rotating the shaft of the motor 120 of the first body 100 clockwise is provided to the motor 120, the body of the motor 120 is rotated counterclockwise. Thus, through the principle in which the first legs 101 are folded (see FIGS. 7A and 7B), the first legs 101 are folded as illustrated in FIG. 8B.

Meanwhile, if the body of the motor 120 is rotated, the second cylinder 140 is rotated together. Therefore, the key 141 adhered closely to the right wall of the key groove 114 as illustrated in FIG. 7A is adhered closely to the left wall of the key groove 114 as illustrated in FIG. 7B. As such, if the key 141 is adhered closely to the left wall of the key groove 114, the second cylinder 140 is not rotated any more. If the second cylinder 140 is not rotated any more, the body of the motor 120 fixed to the second cylinder 140 is also not rotated any more.

Figure 8F:
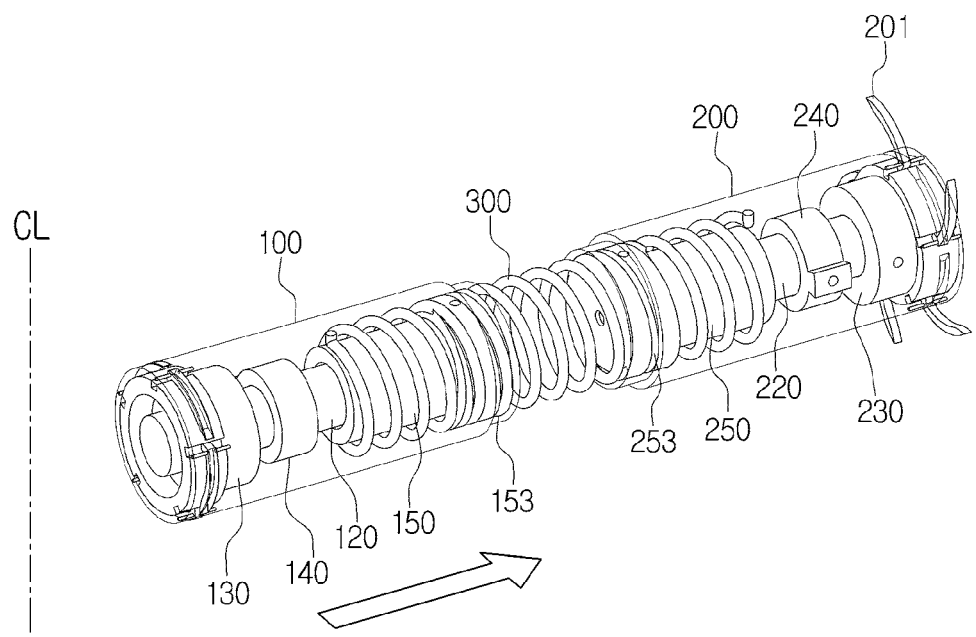

In this case, if the power for rotating the shaft of the motor 120 of the first body 100 clockwise is continuously provided to the motor 120, the shaft of the motor 120 is rotated clockwise because the rotation of the body of the motor is constrained. If the shaft of the motor 120 is rotated, the spring screw 150 is rotated together, and the connection member 300 is accommodated into the internal space of the cover along the screw thread 153 formed at the spring screw 150 as illustrated in FIG. 8F (see the above descriptions regarding FIGS. 3A and 3B). Thus, the length of the connection member 300 exposed between the first and second bodies 100 and 200 is contracted.

In this case, the second legs 201 of the second body 200 support the inner wall of the internal organ (not shown). Therefore, if the length of the connection member 300 is contracted, the first body 100 is relatively moved forward in the arrow direction.

Figure 8G:
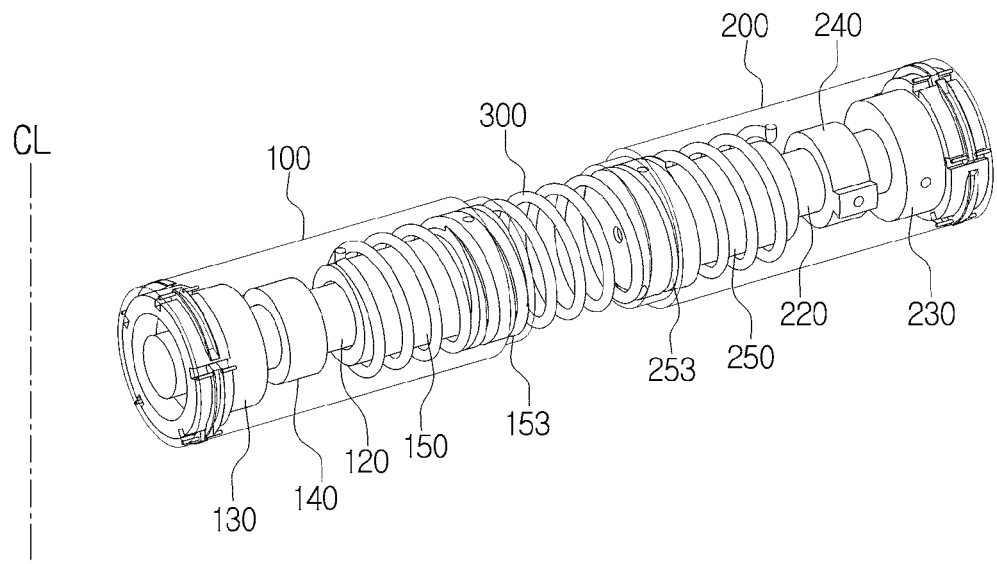

In this state, if the second legs 201 are folded by driving the motor 220 of the second body 200, the robot system 100 returns to the state identical to the initial state (FIG. 8A) as illustrated in FIG. 8G.

When the robot system 100 is continuously moved forward, the aforementioned processes are repeatedly performed.

FIGS. 9A, 9B, 9C, 9D, 9E, 9F, and 9G are perspective views illustrating an operation in which the robot system 10 is moved backward according to this embodiment.

Figure 9A:
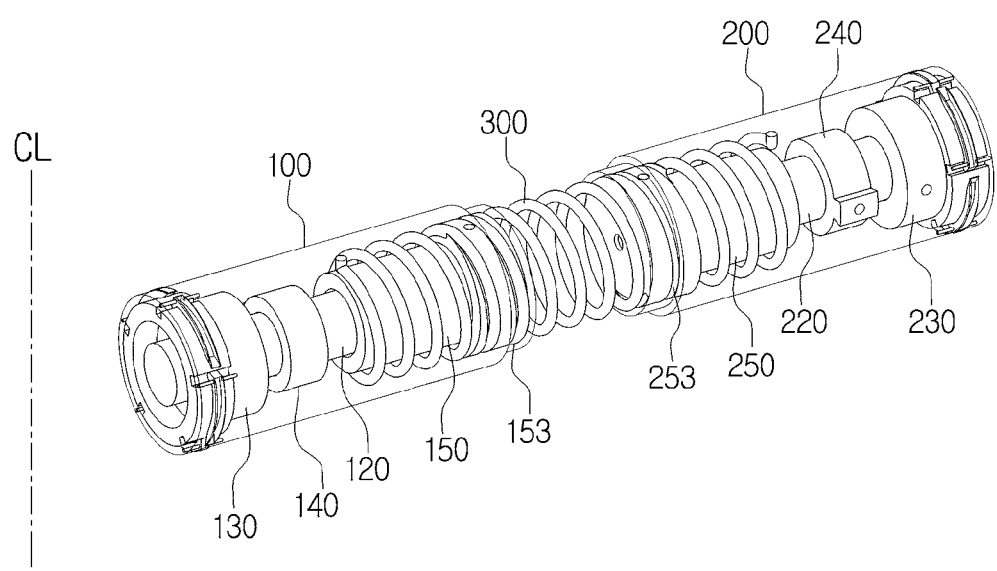
FIGS. 9A, 9B, 9C, 9D, 9E, 9F, and 9G are perspective views illustrating an operation in which the robot system 10 is moved backward according to this embodiment.
Figure 9B:
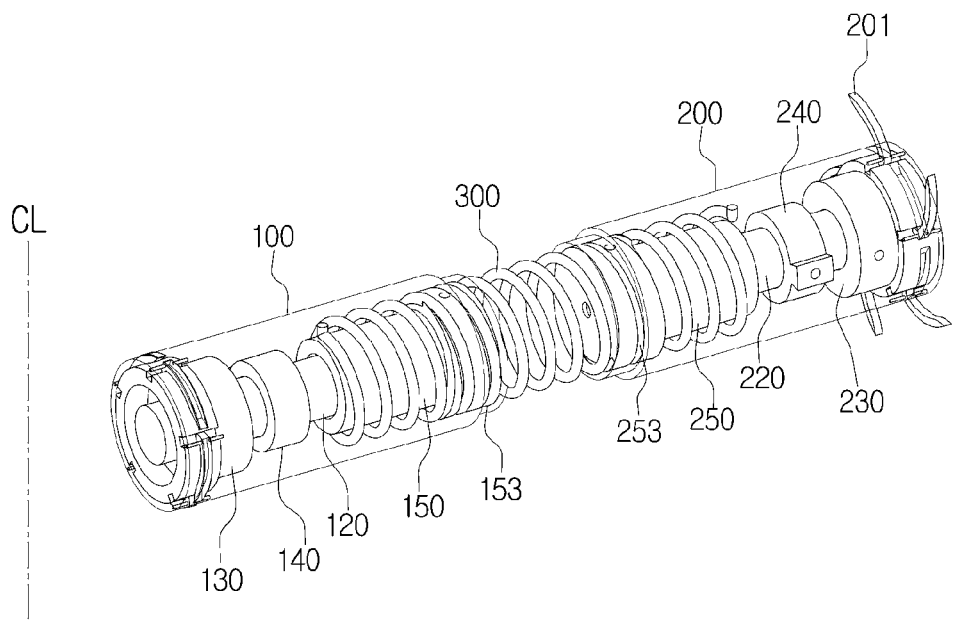

As illustrated in FIG. 9A, power for rotating a shaft of the motor 220 of the second body 200 is provided to the motor 220 so that the robot system 10 in an initial state is moved backward. At this time, the frictional force acts between the connection member 300 and a screw thread 253. Therefore, if the power for rotating a shaft of the motor 220 of the second body 200 is provided to the motor 220, a body of the motor 220 is relatively rotated in the opposite direction. If the body of the motor 220 is rotated, a first cylinder 230 of the second body 200 is rotated, and thus, the second legs 201 are unfolded to support an inner wall of the internal organ (not shown) as illustrated in FIG. 9B.

The structure of the second body 200 is identical to that of the first body 100. Therefore, if the body of the motor 220 is rotated, a second cylinder 240 fixed to the body of the motor 220 is rotated together, and the rotation of the first cylinder 230 is constrained by a key groove provided to a cover of the second body 200. If the second cylinder 240 is not rotated any more, the body of the motor 220 fixed to the second cylinder 240 is also not rotated any more.

Figure 9C:
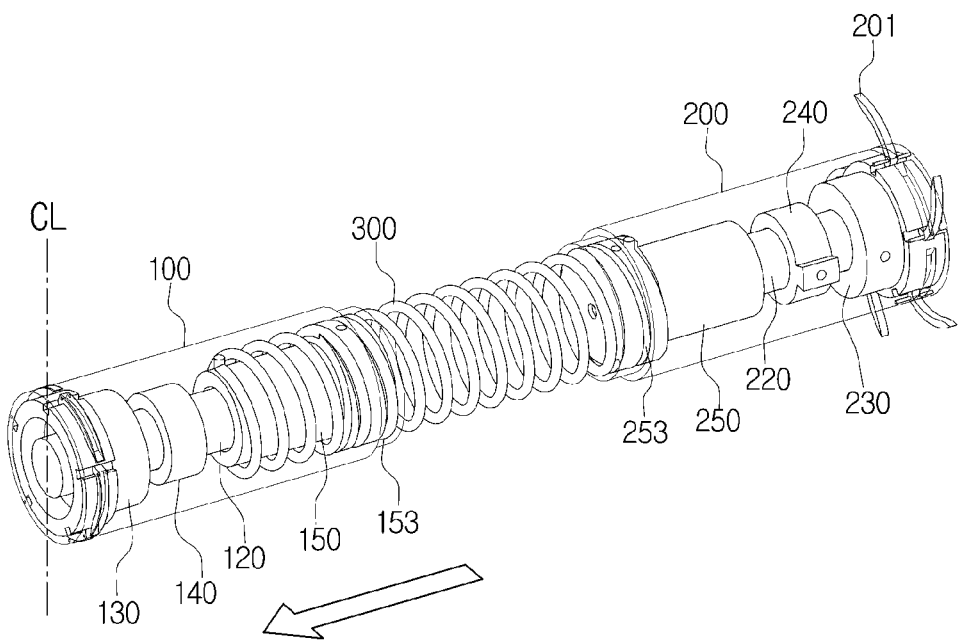

In this case, if the power for rotating the shaft of the motor 220 of the second body 200 is continuously provided to the motor 220, the shaft of the motor 220 is rotated because the rotation of the body of the motor 220 is constrained. If the shaft of the motor 220 is rotated, a spring screw 250 is rotated together. As illustrated in FIG. 9C, the connection member 300 is moved backward along the screw thread 253 formed at the spring screw 250, and thus, the length of the connection member 300 exposed between the first and second bodies 100 and 200. If the length of the connection member 300 is extended, the first body 100 connected to the end portion of the connection member 300 is also moved backward in the arrow direction.

Figure 9D:
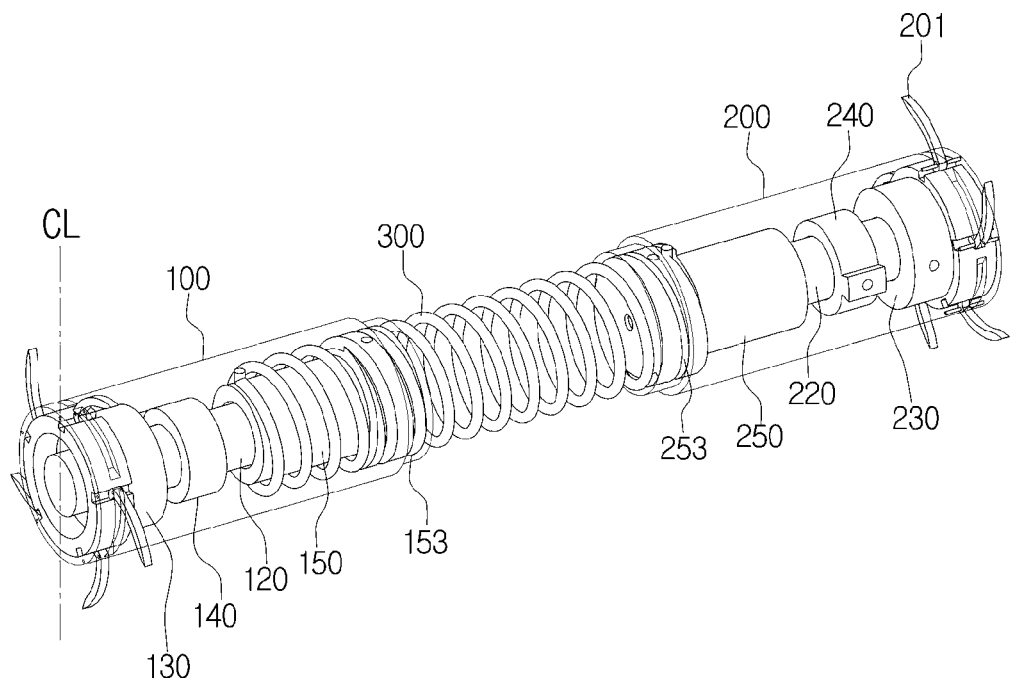

If the connection member 300 is completely extended, the first legs 101 are unfolded by driving the motor 120 provided to the first body 100 as illustrated in FIG. 9D. If the first legs 101 are unfolded, they support an inner wall of the internal organ (not shown).

Figure 9E:
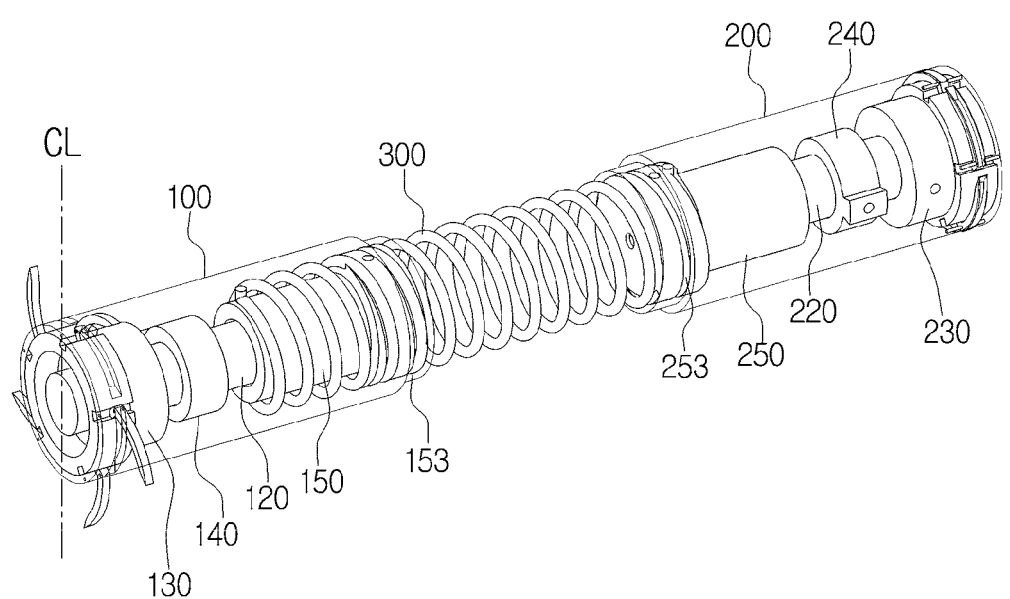

In this state, the power for rotating the shaft of the motor 220 of the second body 200 is provided to the motor 220, and thus, the second legs 201 are folded as illustrated in FIG. 9E.

Figure 9F:
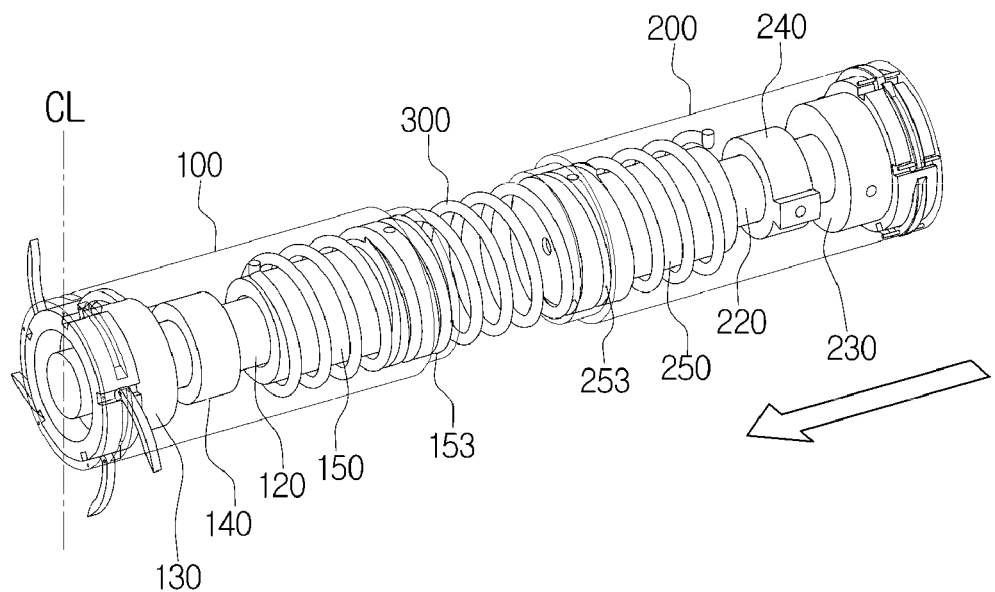

Thereafter, if the power for rotating the shaft of the motor 220 of the second body 200 is continuously provided to the motor 220, the spring screw 250 is rotated, and the connection member 300 is accommodated into the internal space of the cover along the screw thread 253 formed at the spring screw 250 as illustrated in FIG. 9F.

In this case, the first legs 101 of the first body 100 support the inner wall of the internal organ (not shown). Therefore, if the length of the connection member 300 is contracted, the second body 200 is relatively moved backward in the arrow direction.

Figure 9G:
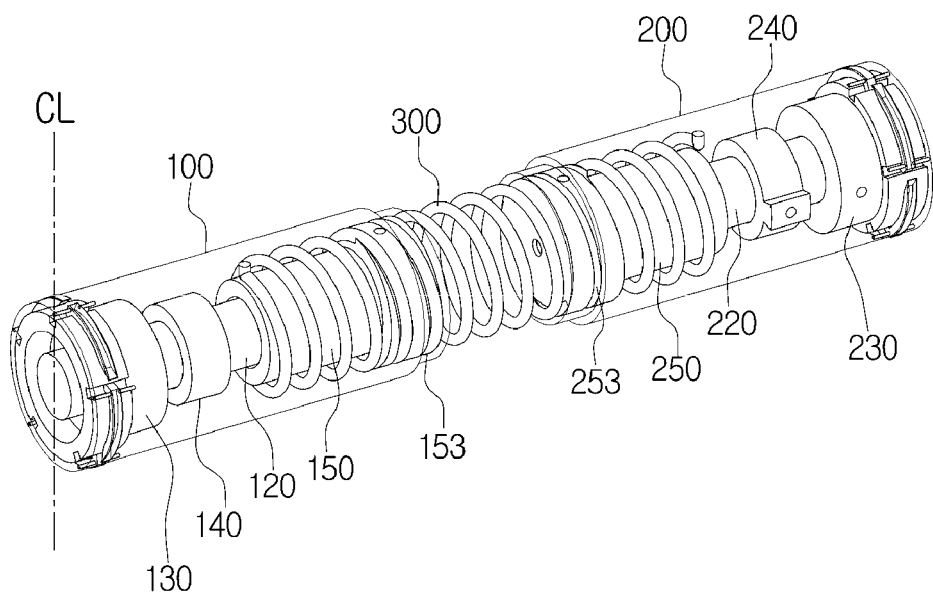

In this state, if the first legs 101 are folded by driving the motor 120 of the first body 100, the robot system 100 returns to the state identical to the initial state (FIG. 9A) as illustrated in FIG. 9G.

When the robot system 100 is continuously moved backward, the aforementioned processes are repeatedly performed.

As described above, in the robot system 100 according to this embodiment, the legs are folded or unfolded using the motors respectively provided to the first and second bodies 100 and 200, and the length of the connection member 300 is extended or contracted. That is, the bidirectional moving of the robot system 100 can be implemented using only the two motors. Accordingly, the robot system 100 according to this embodiment is advantageous in that its structure is simple and its control is easy.

Figure 10:
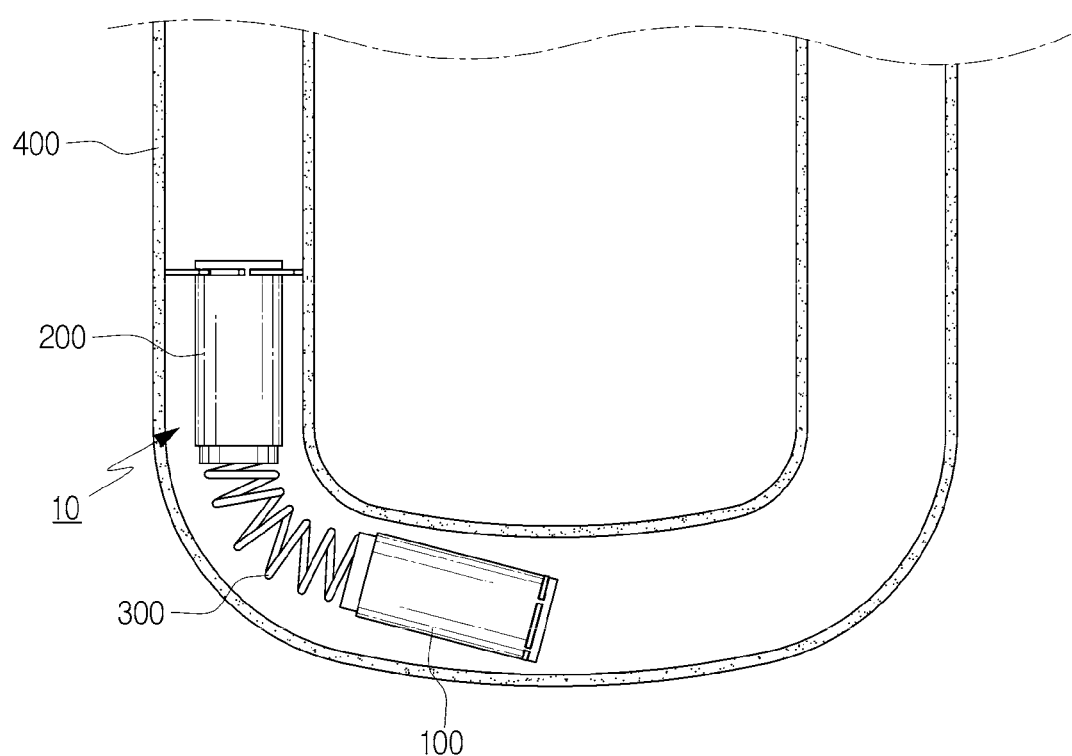
FIG. 10 is a view illustrating the robot system 10 that passes through a bent section of an internal organ 400 according to this embodiment.

FIG. 10 is a view illustrating the robot system 10 that passes through a bent section of an internal organ 400 according to this embodiment.

According to this embodiment, the connection member 300 is configured to be flexibly bent. As described above, the connection member 300 of this embodiment is a coil-type spring. That is, the connection member 300 can be flexibly bent to some degree due to elasticity and then restored in the original state. As such, the connection member 300 has the structure that can be flexibly bent, so that the robot system 10 can be smoothly moved even when it passes through a space with bent sections, such as the internal organ 400, as illustrated in FIG. 10. When the robot system 10 is applied to an endoscope robot system and the like, pain felt by a patient subjected to a surgical operation can be reduced.

The bidirectional moving micro-robot system disclosed herein can move forward and backward in the inside of internal organs. Since the capsule type micro-robot bidirectional moving system rapidly moves in the inside of the internal organ, it can effectively perform desired photographing or operation.

While the present invention has been described in connection with certain exemplary embodiments, it is to be understood that the invention is not limited to the disclosed embodiments, but, on the contrary, is intended to cover various modifications and equivalent arrangements included within the spirit and scope of the appended claims, and equivalents thereof.

What is claimed is:

1. A bidirectional moving micro-robot system comprising:
   a first body having a plurality of legs foldably/unfoldably connected thereto;
   a second body having a plurality of legs foldably/unfoldably connected thereto; and
   a connection member having both end portions respectively connected to the first and second bodies,
   wherein the structure of the second body is identical to the structure of the first body;
   wherein a first motor in the first body or a second motor in the second body is driven to control the length of the connection member so that the micro-robot system is moved in a forward or backward direction;
   wherein a first spring screw is connected to a first shaft of the first motor, a second spring screw is connected to a second shaft of the second motor, the first spring screw is fastened to the connection member through a first screw thread formed on an outer circumferential surface of the first spring screw, and the second spring screw is fastened to the connection member through a second screw thread formed on an outer circumferential surface of the second spring screw; and
   wherein the length of the connection member exposed between the first and second bodies is controlled as the connection member is moved along the first screw thread or the second screw thread by rotation of the first shaft of the first motor or the second shaft of the second motor.

2. The bidirectional moving micro-robot system according to claim 1, wherein the connection member is flexibly bent.

3. The bidirectional moving micro-robot system according to claim 2, wherein the connection member is a coil-type spring.

4. The bidirectional moving micro-robot system according to claim 3, wherein the first body comprises:
   a first cylinder connected to the first motor to surround a body of the first motor; and
   a cover for accommodating the first motor and the first cylinder in the interior thereof, wherein:
   a plurality of leg latching grooves are formed at an outer circumferential surface of the first cylinder;
   the plurality of legs connected to the first body are radially disposed about the central axis of the first body, and each of the legs is hinge-fixed to the cover; and
   as the first cylinder is rotated by the rotation of the body of the first motor, an end portion of each of the legs connected to the first body is latched by the interference of each of the leg latching groove so that the legs are folded or unfolded.

5. The bidirectional moving micro-robot system according to claim 4, wherein:
   the first body further comprises a second cylinder connected to the first motor to surround the body of the first motor;
   a key is formed to protrude from an outer circumferential surface of the second cylinder;
   a key groove engaged with the key is formed at an inner circumferential surface of the cover; and
   the width of the key groove is wider than that of the key.

6. The bidirectional moving micro-robot system according to claim 5, wherein an anti-rotation groove is formed in the length direction of the cover at the inner circumferential surface of the cover, and an anti-rotation projection engaged with the anti-rotation groove is formed at each end of the coil-type spring.

7. The bidirectional moving micro-robot system according to claim 6, wherein, when the length of the connection member is contracted, a portion of the coil-type spring is accommodated into the interior of the cover.

8. The bidirectional moving micro-robot system according to claim 7, wherein the first and second bodies are disposed to be symmetric to each other about the connection member.

9. The bidirectional moving micro-robot system according to claim 8, wherein the length of the connection member is controlled by the first motor provided to the first body when the bidirectional moving micro-robot system is moved forward, and the length of the connection member is controlled by the second motor provided to the second body when the bidirectional moving micro-robot system is moved backward.

* * * * *